United States Patent [19]

Johal

[11] Patent Number: 5,043,287

[45] Date of Patent: Aug. 27, 1991

[54] RECOVERY OF WATER SOLUBLE BIOPOLYMERS FROM AN AQUEOUS SOLUTION BY EMPLOYING A POLYOXIDE

[75] Inventor: S. S. Johal, Sagamore Hills, Ohio

[73] Assignee: The Standard Oil Company, Cleveland, Ohio

[21] Appl. No.: 353,138

[22] Filed: May 16, 1989

[51] Int. Cl.⁵ .............................................. G01N 1/18
[52] U.S. Cl. .................................... 436/177; 435/814; 436/175; 436/825; 536/127
[58] Field of Search ................ 435/101, 814; 436/825, 436/175, 177; 536/102, 127, 124

[56] References Cited

U.S. PATENT DOCUMENTS

| | | | |
|---|---|---|---|
| 4,126,605 | 11/1978 | Schneider et al. | 424/85 |
| 4,746,511 | 5/1988 | Kobatake et al. | 424/92 |
| 4,835,257 | 5/1989 | Friedrich-Fiechtl et al. | 530/387 |

OTHER PUBLICATIONS

Soini et al, Clin. Chem. 25/3, 353–361 (1979).

*Primary Examiner*—Amelia Burgess Yarbrough
*Attorney, Agent, or Firm*—Larry W. Evans; Joseph G. Curatolo; Teresan W. Gilbert

[57] ABSTRACT

The instant invention is a process for the recovery from an aqueous solution of water soluble biopolymers, in particular polysaccharides, gums, agar, agarose and starches by the addition of polyoxide solution to the biopolymer containing solution. The biopolymer is then separated and collected.

29 Claims, No Drawings

_5,043,287_

RECOVERY OF WATER SOLUBLE BIOPOLYMERS FROM AN AQUEOUS SOLUTION BY EMPLOYING A POLYOXIDE

BACKGROUND

This application is related to U.S. patent application Ser. No. 294,153 entitled "Recovery of Glucan by a Divalent Cation Salt in Concert With a Water Miscible Organic Solvent," and U.S. patent application Ser. No. 294,250 entitled "Recovery of Glucan by Employing a Divalent Cation at an Alkaline pH".

The invention relates to a process for the recovery of water soluble biopolymers, in particular polysaccharides, gums, agar, agarose and starch. Further, the invention relates to the recovery of the biopolymers in a solution by adding a polyoxide, in particular polyethylene glycol or polyethylenesorbitan to the biopolymer containing liquid to induce precipitation of the biopolymer.

Many species of bacteria, fungi, plants and algae produce water soluble polysaccharides, gums and starches. Polysaccharides produced by fungi and bacteria generally are obtained by fermentation processes. The biopolymers are then recovered from the broth solution. Biopolymers such as polysaccharides produced by algae, are intracellular macromolecules which are extracted from naturally occurring fresh water or marine mixed cultures. Natural biopolymer gums such as locust bean gum and guar gum are produced and harvested from shrubs and trees generally found in Africa, Asia and India. Typically, the gum is found in the seeds of the plants. The crude gum powder can be hydrated or suspended and then the gum is precipitated from the solution.

The full commercial potential of biopolymers is restricted by high price and costs due to processing and product recovery. Downstream processes, especially in fermentations are usually a multistep batch process that use solvents to precipitate the biopolymer from the broth or solution. Current procedures teach the use of a water miscible organic solvents such as isopropyl alcohol or acetone for the recovery of biopolymers such as water soluble polysaccharides, in particular glucan from fermentation media and other glucan containing solutions. As practiced, the clarified media is concentrated to a flowable viscosity and precipitated with greater than 50% by volume solvent. The precipitate is drained and then successively treated with higher concentrations of the water miscible organic solvent. In the case of glucan-type polysaccharides a minimum of 2 to 3-fold excess of solvent to broth is generally required to adequately precipitate all of the glucan in solution. Alternatively, usable glucans can be recovered and concentrated by more elaborate techniques such as freeze-drying, lyopholization or spray-drying at moderate temperatures of about 150° to 180° C.

U.S. Pat. No. 3,759,896 discloses a process to produce polysaccharides with anti-tumor activity mainly consisting of B-(1->3)-linked D-glucose residue by obtaining culture filtrates of fungi belonging to Ascomycetes, Basidiomycetes and Fungi imperfect and then purifying the culture filtrate by sequential treatments of acidification, deionization by ion exchange resins and precipitation with a water soluble miscible solvent.

U.S. Pat. No. 4,072,567 discloses a process for producing a glucan by cultivating a Streptococcus microorganism in a liquid medium and recovering the glucan by sedimentation, filtration or sieving. The crude glucan is further processed by dissolving in sodium hydroxide, centrifuging, neutralizing with hydrogen chloride and then washing.

Xanthan gum, an anionic polysaccharide, is a fermentation product of the bacteria _Xanthomonas campestris_. The polysaccharide is recovered from the fermentation broth by salt precipitation. Known precipitating agents for the polysaccharide include quarternary amine salt precipitation (U.S. Pat. No. 3,119,812); aluminum salt precipitation (U.S. Pat. No. 4,051,317); amine salt precipitation (U.S. Pat. No. 4,254,257) and alkaline precipitation in the presence of divalently cations (U.S. Pat. No. 3,382,229). Known precipitating agents for polysaccharides are calcium ion combined with an alkaline pH, isopropyl alcohol and a quarternary compound, see U.S. Pat. No. 4,053,699.

This invention provides a process for large scale purification and recovery of water soluble biopolymers from a variety of aqueous solutions. It has the advantages of being cost efficient, scalable from laboratory to large process scale and no harsh or hazardous chemicals.

The water soluble biopolymers of polysaccharides, gums and starches are widely used in industrial and food applications. The biopolymers have useful properties such as stability in cold, hot or high salt environments, performance at low concentrations and pseudoplasticity. Applications of the biopolymers in the industrial area include uses as a suspending agent, viscosifier, stabilizer and emulsifier. Applications of the biopolymers in the food industry include uses to improve body and texture, thickening powder, gel stability and emulsification.

It is an object of the instant invention to recover water soluble biopolymers from aqueous solutions. It is another object of the instant invention to recover biopolymers such polysaccharides, gums, agars, agaroses and starches from solution by precipitating the biopolymer from the solution with a polyoxide, such as polyethylene glycol or polyoxyethylenesorbitan.

These and other objects, together with the advantages over known methods shall become apparent from the specification which follows and are accomplished by the invention as herein described and claimed.

SUMMARY OF THE INVENTION

The instant invention is a process for the recovery of water soluble biopolymers such as polysaccharides, gums, agar, agarose and starches from an aqueous solution containing the biopolymers by adding a polyoxide such as polyethylene glycol or polyoxyethylenesorbitan to precipitate the biopolymers from solution. The biopolymer is then collected.

DETAILED DESCRIPTION OF THE INVENTION

The process of the instant invention is to recover water soluble biopolymers from an aqueous solution by adding a polyoxide, in particular polyethylene glycol or polyoxyethylenesorbitan which induces precipitation of the biopolymers. The biopolymers can be collected, further purified and concentrated.

The process involves bringing the solution of water soluble biopolymers into contact with a polyoxide, such as polyethylene glycol or polyoxyethylenesorbitan. The solution of water soluble biopolymers may be clarified or unclarified of cell biomass and extraneous debris. Further, the solution may contain a single type of biopolymer or more than one type of biopolymer.

Generally, the type of biopolymers that can be recovered from solution by the instant invention are water soluble and include but are not limited to water soluble polysaccharides, gums, agars, agaroses, starches and the like.

Organisms that produce water soluble polysaccharides are filamentous fungi, bacteria and the like. Exemplary water soluble polysaccharides include but are not limited to glucans, scleroglucan, schizophyllan and the like. Generally, a glucan is defined as a polysaccharide substance composed of glucose and is characterized by 1-3 linked D-glycosyl units. Scleroglucan and schizophyllan are nonionic homopolysaccharides which are characterized as a linear chain of 1-3-linked D-glycosyl units with about 30 to about 35% of the linear chain containing single D-glycosyl units which are attached by 1-6 linkages. The average molecular weight is greater than or equal to $5 \times 10^6$. The chains are self-associated in a triple helix arrangement.

Typical filamentous fungi that produce nonionic polysaccharides, in particular glucan, include but are not limited to organisms belonging to the genus Sclerotium, Sclerotinia, Corticum, Helotium, Stromatinia, Claviceps and the like. Exemplary organisms which produce glucans include but are not limited to *Sclerotium glucanicum, Sclerotium delphinii, Sclerotium coffeicolum, Schizophyllum commune, Sclerotium rolfsii, Corticium rolsii, Sclerotinia gladod, Stromatinia narcissi* and the like. The organisms listed in Halleck U.S. Pat. No. 3,301,848 and in Komatsu et al. U.S. Pat. No. 3,759,896 are also included as organisms that excrete glucan. Scleroglucan is produced by filamentous fungi of the genera Sclerotium, in particular by *Sclerotium rolfsii, Sclerotium glucanicum, Sclerotium delphinii, Sclerotium coffeicolum* and the like. Schizophyllan is produced by fungi of the genera Schizophyllum, in particular by *Schizophyllum commune*.

Conventional methods are employed in culturing microorganisms for the production of the extracellular water soluble polysaccharides, in particular glucan. Typical cultivation methods employed include but are not limited to batch, fed batch, semi-continuous fermentation, continuous fermentation and the like. In general, the process involves growing the organism, inoculating a batch of fermentable broth with the organism, allowing the organism to ferment and recovering the water soluble polysaccharide from the broth. The aqueous nutrient medium should provide a substrate for the production of the polysaccharide by the organism. The aqueous nutrient medium will normally contain assimilable carbon and nitrogen sources, organic materials and if required, minor organic and inorganic nutrients such as trace salts, trace elements, vitamins, amino acids and the like.

Polysaccharides isolated from algae and/or blue green bacteria can be recovered by the process of the instant invention. These polysaccharides include but are not limited to agar, agarose and the like. Agar is a polysaccharide mixture isolated from certain agar bearing algae, particular red algae of Gelidium and Gracilaria spp. Agarose is purified from agar and agar-containing seaweed and is a linear galactan made up of the basic repeating units agarobiose.

Gums in aqueous solutions can be recovered by the process of the instant invention. Typical, gums include but are not limited to locust bean gum, guar gum and the like. They generally occur as exudations from various trees and shrubs in tropical areas. Generally, gums are defined as a carbohydrate high polymer insoluble in alcohol and other organic solvents but soluble or dispersible in water. Natural gums are hydrophillic polysaccharides composed of monosaccharide units joined by glycosidic bonds.

Starch copolymers recovered by the process of the instant invention include but are not limited to starch-acrylonitrile copolymers.

Biopolymers can be recovered by this process from solutions containing a single kind of biopolymer or a combination of biopolymers. A mixture of different biopolymers can be recovered and concentrated as a single homogeneous population by this process.

The instant invention is directed to the process to recover the biopolymers from solution after the biopolymer has been produced. The biopolymers are generally produced by known methods in the art.

The present invention is directed toward the recovery of the water soluble biopolymers from solution. The solution containing the biopolymer is contacted with a polyoxide. The mixture is then mixed and the biopolymer precipitates out of solution. The precipitated biopolymer is and can be washed, resuspended for further process and/or stored.

Polyoxides are employed to induce precipitation of the biopolymers. Polyoxides include, but are not limited to polyethylene glycol, polyoxyethylenesorbitan and the like. The polyoxide concentration mixed in the aqueous solution containing the biopolymer is in the range from about 3% to about 30%, and preferably about 10% to 15%. A saturated polyoxide solution is the preferred form of addition, however, a dilute polyoxide solution can be employed but the solution volume will be increased.

Any form of polyethylene glycol, for example solid or liquid, can be employed. Average molecular weight of the polyethylene glycol employed is that which is commercially available in the range of about 1,000 to 20,000. Generally about 10% to about 80% (w/v) weight to volume polyethylene glycol solution is employed.

Polyoxyethylenesorbitan is generally obtained as a syrup. The monolaurate form (Tween 20) is the preferred composition, although monooleate (Tween 80), monopalmitate (Tween 40), monostearate (Tween 60) trioleate (Tween 85) and the like are also usable.

The process temperature is in the range of about 15° C. to about 100° C. and preferably 20° C. to 80° C. The process temperature is somewhat dependent upon the thermal stability of the biopolymers.

After the addition of the polyoxide to the biopolymer solution it is then actively mixed resulting in the precipitation of the biopolymer. Upon biopolymer precipitation from solution the viscosity of the solution declines.

The precipitated water soluble biopolymer is collected from the solution by conventional methods such as centrifugation, filtration, decantation and the like. The biopolymer can be further processed and/or purified by known methods such as rehydration, precipitation and the like.

For example, once collected the biopolymer gum or polysaccharide can be rehydrated by addition of water and vigorous agitation for further purification. The purity of the biopolymer may be increased by repeated precipitation. The precipitated biopolymer from this process is easily and readily hydrated and dispersed.

SPECIFIC EMBODIMENTS

The following examples further illustrate the present invention. These embodiments are presented by way of example and not by way of limitation of the scope of the invention.

The polyethylene glycol precipitation procedure employed the following steps (1) a concentrated 20 to 80% w/v aqueous polyethylene glycol solution with a molecular weight range of 3-4,000, 6-8,000 or 20,000 was added to the biopolymer-containing solution at a polyethylene glycol concentration in the range of about 3 to about 15%, (2) the solution was vigorously agitated and upon mixing a white stringy or clumpy precipitate was observed and the viscosity of the solution declined to that of about a 3 to about 15% polyethylene glycol solution (<4 cps at 10.2 sec$^{-1}$), and (3) the biopolymer was collected by one of the following techniques a) spooling onto a rod or other object which provided a surface for the precipitate to adhere to, b) filtration, c) decantation, or d) centrifugation.

The polyoxyethylenesorbitan precipitation process employed the following steps (1) a polyoxyethylenesorbitan monolaurate syrup was added to the biopolymer-containing solution at concentration in the range of about 10 to 30%, (2) the solution was vigorously agitated whereupon the biopolymer precipitated from solution, (3) the biopolymer was then collected from the broth by liquid/solid separation techniques.

EXAMPLE 1

One hundred milliliters of clarified scleroglucan broth which was produced by shake flask fermentation of S. rolfsii and stored at room temperature, was transferred a two hundred fifty milliliter flask. A 40% polyethylene glycol 8000 solution prepared with distilled water was added to broth resulting in a final polyethylene glycol concentration in the mixture of about 4.5%. The solution was then vigorously agitated. Within one or two minutes a white precipitate was observed. Upon the appearance of the precipitate the viscosity of the solution declined to that of about water. The precipitate was recovered by filtering through a large pore strainer. About one-hundred and five milliliters of solution was recovered after the scleroglucan precipitate was separated.

This procedure was done using less than a 3% polyethylene glycol solution, but no precipitate was obtained.

EXAMPLE 2

Fourteen milliliters of polyethylene glycol 4000 was added to a 100 milliliter sample of fermentation broth as used in example 1. The results were identical as to when polyethylene glycol 8000 was employed in example 1. The procedure was also done using about a 5% and about a 7% polyethylene glycol solution both resulting in precipitation of the scleroglucan.

EXAMPLE 3

About 70 milliliters of concentrated unclarified shake flask grown S. rolfsii broth, was obtained after about 72 hours of fermentation, and then was diluted with about 100 milliliters of distilled water to improve pouring, handling and mixing. It was then homogenized at a high speed for about 30 seconds in a Waring blender to break up the micelles.

About 165 milliliters of homogenized broth was recovered. About 25 milliliters was set aside as a control sample to compare viscosities. About 25 milliliters of about 40% polyethylene glycol 8000 solution was added the remaining 140 milliliters and the solution mixed. A biomass-glucan composite precipitated out of solution resulting in a clear non-viscous solution. The solution was decanted and the precipitate blotted with a paper towel. The moist precipitate was then immersed in about 20 milliliters of ethanol. The ethanol was decanted and the precipitate again blotted dry with a paper towel and pressed into a thin sheet. The firm, thin white sheet of scleroglucan and fungal biomass which was dry to the touch was cut into a number of small pieces with a pair of scissors. This biopolymer material weighed about 3.52 grams.

The precipitate was solubilized by transferring the clumps to a 250 milliliter flask and adding about 20 milliliters of cold distilled water. The flask was vigorously agitated for about 5 minutes. Much of the white stringy precipitate hydrated to form an opaque gel-like material. About another 20 milliliters of cold distilled water was added and then an additional 100 milliliters of boiling water was then added to the scleroglucanfungal biomass blend. The material readily hydrated and the viscosity developed within about 15 minutes. The flask was transferred to a rotary shaker and agitated at about 350 revolutions per minute, at room temperature, for about 18 hours. After about 18 hours, most of the precipitate, except for a few large clumps, had resuspended and the following viscosities were obtained.

Control (non-precipitated sample): 745 cps (10.2 sec$^{-1}$)

Precipitated sample: 712 cps (10.2 sec$^{-1}$)

This example demonstrates that the biopolymer is not denatured by the recovery process of the instant invention. The polyethylene glycol does not interfere with the biopolymer because it can be rehydrated.

EXAMPLE 4

About 1% solutions of guar gum and locust bean gum purchased from Sigma Chemical Co., St. Louis, Mo. were prepared by hydrating the gums in distilled water and agitating for at least 16 hours on a rotary shaker, at 350 revolutions per minute, at room temperature. The biopolymers were well-dispersed as evidenced by the absence of microgels, although all of the samples contained quantities of insoluble materials. Microscopic examination revealed that these materials were cell debris and other particulate matter.

About 20 milliliters of each 1% biopolymer gum solution was transferred to a separate test tube, at room temperature. About 5 milliliters of a 40% polyethylene glycol 8000 solution which was prepared in distilled water was then added to each sample. The samples were vortexed and left at room temperature for about 5 minutes.

A precipitate appeared in the guar gum and locust bean gum samples and within about 40 minutes the precipitate had settled at the bottom of the tube and viscosity of the solutions had declined to that slightly greater than water. Guar gum and locust bean gum behave like scleroglucan and are recovered by polyethylene glycol-induced precipitation.

EXAMPLE 5

Agarose, available from BRL agarose, and agar available from Difco Bacto Agar, were each separately made into about 1% solution in water. About a 10 ml. sample of each 1% agar and agarose solution was transferred to a separate test tube. About 0.8 ml of a 70% polyethylene glycol 8000 solution was added to each test tube. The test tubes were vortexed vigorously and left at room temperature for about 5 minutes. Within about 5 minutes a precipitate appeared in both samples. Agarose and agar are precipitated by this process employing polyethylene glycol.

EXAMPLE 6

Potato starch, available from Sigma Chemical, was made into about a 5% solution in water. About a 10 ml. sample of the potato starch was transferred to a test tube. About 0.8 ml of a 40% polyethylene glycol solution was added. A precipitate was observed upon addition of the polyethylene glycol solution.

EXAMPLE 7

About 20 milliliters of shake flask cultured, particulate-free scleroglucan broth was put in a fifty milliliter test tube. About 3 milliliters of undiluted polyoxyethylene-sorbitan monolaurate (Tween 20) purchased from Sigma Chemical Company, St. Louis, Mo. was added to the test tube. The tube was vigorously vortexed, a precipitate was observed and the tube was vortexed again. The tube was placed on the bench, whereupon a scleroglucan flocculant was observed. The flocculated scleroglucan had a stringy appearance similar to the polyethylene glycol precipitated biopolymer. The biopolymer was collected and washed with ethanol. When added back to water, the biopolymer solubilized immediately.

Although the invention has been described in detail through the preceding examples, these examples are for the purpose of illustration only and it is understood that variations and modifications can be made by one skilled in the art without departing from the spirit and the scope of the invention.

We claim:

1. A process for the recovery of biopolymers comprising adding polyoxide glycol to an aqueous solution containing water soluble biopolymers and then mixing the biopolymer polyoxide solution resulting in the precipitation of the biopolymer wherein the biopolymer is selected from the group consisting of water soluble polysaccharides, gums, agar, agarose, starches and combinations thereof.

2. A process for the recovery of biopolymers from an aqueous solution comprising adding a polyoxide to precipitate a water soluble biopolymer from solution wherein the biopolymer recovered is selected from the group consisting of water soluble polysaccharides, gums, agar, agarose, starches and combinations thereof from solution.

3. The process of claim 1 wherein the polyoxide is selected from the group consisting of polyethylene glycol, polyoxyethylenesorbitan and combinations thereof.

4. The process of claim 1 wherein the biopolymer solution is clarified or unclarified of biomass or extraneous debris.

5. The process of claim 1 wherein the water soluble polysaccharides are selected from the group consisting of glucan, scleroglucan, schizophyllan and combinations thereof.

6. The process of claim 1 wherein the gums are selected from the group consisting of locust bean gum, guar gum and combinations thereof.

7. The process of claim 1 wherein the gums are natural gums.

8. The process of claim 1 wherein the starch is selected from the group consisting of starch copolymers, starchacrylonitrile copolymers and combinations thereof.

9. The process of claim 1 wherein there is a single kind of biopolymer in the solution.

10. The process of claim 1 wherein there is a combination of biopolymers in the solution.

11. The process of claim 1 wherein the solution containing the biopolymer is contacted with the polyoxide solution and mixed vigorously to induce the precipitation of the biopolymer from the solution.

12. The process of claim 1 wherein the biopolymer is recovered.

13. The process of claim 2 wherein the polyoxide is selected from the group consisting of polyethylene glycol, polyoxyethylenesorbitan and combinations thereof.

14. The process of claim 1 wherein the polyoxide is polyethylene glycol.

15. The process of claim 1 wherein the polyoxide is polyoxyethylenesorbitan.

16. The process of claim 14 wherein the polyethylene glycol is available in the range of 1,000 to 20,000 molecular weight.

17. The process of claim 1 wherein the polyoxide concentration is in the range from about 3% to about 30%.

18. The process of claim 17 wherein the polyoxide concentration is in the range from about 10% to about 15%.

19. The process of claim 14 wherein the polyethylene glycol concentration is in the range from about 3% to about 15%.

20. The process of claim 15 wherein the polyoxyethylenesorbitan solution is in the range from about 10% to about 30%.

21. The process of claim 1 wherein the process occurs at a temperature in the range of about 15° C. to about 100° C.

22. The process of claim 1 wherein the process occurs at a temperature in the range of about 20° C. to about 80° C.

23. The process of claim 1 wherein the precipitated water soluble biopolymer is collected from solution by methods selected from the group consisting of centrifugation, filtration, decantation and combinations thereof.

24. The process of claim 24 wherein the collected biopolymer is further processed by methods selected from the group consisting of rehydration, precipitation and combinations thereof.

25. A water soluble biopolymer collected from an aqueous solution comprising adding a polyoxide wherein the polyoxide is selected from the group consisting of polyethylene glycol, polyoxyethylenesorbitan and combinations thereof to an aqueous solution containing water soluble biopolymer and then mixing the biopolymer polyoxide solution which results in the precipitation of the biopolymer wherein the biopolymer is selected from the group consisting of water soluble polysaccharides, gums, agar, agarose, starches and combinations thereof.

26. The process of claim 25 wherein the polyoxide is selected from the group consisting of polyethylene glycol, polyoxyethylenesorbitan and combinations thereof.

27. The process of claim 1 wherein the biopolymer precipitated is selected from the group consisting of schleroglucan, schizophyllan and combinations thereof.

28. The process of claim 2 wherein the biopolymer precipitated is selected from a group consisting of schleroglucan, schizophyllan and combinations thereof.

29. The process of claim 1 wherein the biopolymer precipitated is schleroglucan.

* * * * *